United States Patent

Krausz et al.

[11] 4,141,971
[45] Feb. 27, 1979

[54] DERIVATIVES OF MIDECAMYCINE

[75] Inventors: Francois Krausz; Alain Calvet, both of Montpellier, France

[73] Assignee: C M Industries, Paris, France

[21] Appl. No.: 701,291

[22] Filed: Jun. 30, 1976

[30] Foreign Application Priority Data

Jul. 8, 1975 [FR] France .................................. 75 21432

[51] Int. Cl.² ............................................. A61K 31/70
[52] U.S. Cl. ....................................... 424/180; 536/9; 536/17
[58] Field of Search .................. 536/9, 10, 11, 12, 14, 536/15, 17; 424/180

[56] References Cited

U.S. PATENT DOCUMENTS 3,040,025  6/1962  Murphy et al. ........................... 536/9
3,661,891  5/1972  Sinkula ..................................... 536/9

OTHER PUBLICATIONS

Inouye et al., J. of Antibiotics, Jul. 1971, vol. 24, pp. 460–471.
Journal of Antibiotics, vol. 24, Jul.–Dec., 1971, pp. 457 and 480 (Table 4).
Journal of Antibiotics, vol. 29, No. 5, May, 1976, Japan Antibiotics Res. Assoc., pp. 536–548.

Primary Examiner—Richard Raymond
Attorney, Agent, or Firm—Fulwider, Patton, Rieber, Lee & Utecht

[57] ABSTRACT

Novel derivatives of midecamycine, of the formula:

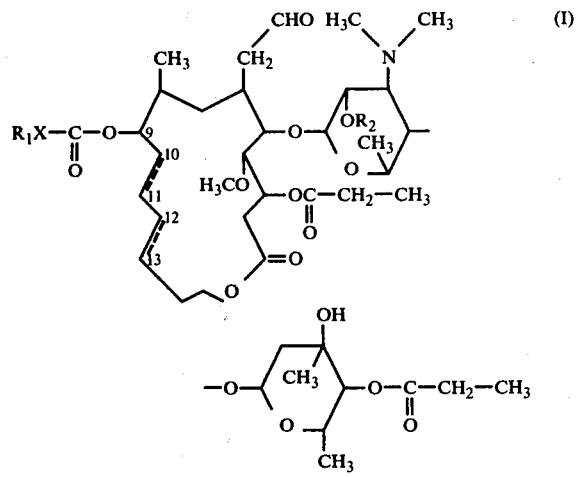

wherein X represents an oxygen atom or a sulphur atom, $R_1$ represents a straight or branched alkyl group, an alkenyl group or an aryl group, $R_2$ represents a hydrogen atom or a lower acyl group, the dotted lines represent the possible presence of double bonds, it being understood that the 2 double bonds at the 10,11 position on the one hand and the 12,13 position on the other either exist simultaneously or neither of them exists, which give by oral administration plasma rates which are higher than midecamycine and which lack its bitter taste, together with their process of preparation.

17 Claims, No Drawings

DERIVATIVES OF MIDECAMYCINE

The present invention relates to derivatives of an antibiotic given the name Midecamycine and corresponding to the formula:

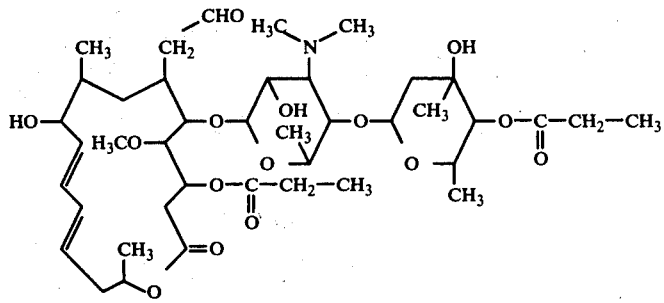

The invention seeks to provide substances having an antibiotic activity which is utilisable in human or veterinary medicine.

The new compounds correspond to the general formula:

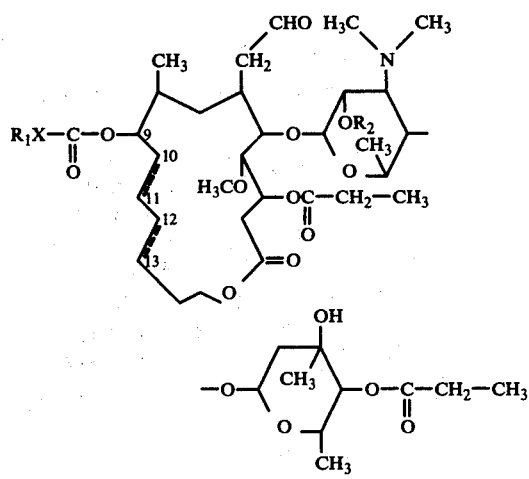

in which X represents an O or S atom, $R_1$ represents a straight or branched alkyl group, an alkenyl group or an aryl group, and $R_2$ represents an H atom or an acyl group.

The broken lines indicate the possible presence of double bonds, it being understood that the two double bonds 10,11 on the one hand and 12,13 on the other either exist simultaneously or neither of them exists.

These new compounds have the following important advantages in comparison with Midecamycine:

They have in vitro at least equal activity as regards various Gram+ bacteria;

In vivo, they give in equal dosages a better protection against experimental disorders;

They provide higher plasmatic rates after administration orally;

They lack the very strong bitter taste of Midecamycine.

The compounds (I) in which $R_2 = H$ are obtained from Midecamycine by the action in pyridine of a chloroformate or thiochloroformate of the formula:

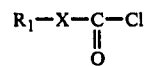

where X represents an O or S atom and $R_1$ is as defined above, at a somewhat elevated temperature (0°-25° C.).

By replacing Midecamycine with tetrahydromidecamycine, a known compound, the derivatives (I) are obtained which do not have double bonds at 10,11 and 12,13. Isolation of the compounds is effected by dilution with water, followed by extraction with a suitable organic solvent such as ethyl acetate. The crude product so obtained, if it appears necessary, can be purified by chromatography on silica or alumina followed, if required, by crystallisation from an appropriate solvent.

The compounds (I) in which $R_2 = $ acyl are obtained from compounds in which $R_1 = $ H by the action of the acid anhydride $(R_2CO)_2O$ in pyridine under reflux.

The following examples illustrate the results obtained:

EXAMPLE 1

9-Methoxycarbonyl midecamycine of Formula (I) above, in which $R_1 = CH_3$, $X = O$, $R_2 = H$.

15 g of Midecamycine was dissolved in 120 ml of pyridine and then the solution was cooled in an ice bath and 30 ml of methyl chloroformate was added dropwise. After the end of the addition, the mixture was left for 24 hours under agitation at the ambient temperature. The solution was diluted with 500 ml of water and then extracted 3 times with 150 ml of ethyl acetate.

The organic phase was successively washed:
with a dilute hydrochloric solution until the pH of the wash solutions equalled 4;
with 150 ml of a saturated sodium bicarbonate solution;
with 150 ml water;
with 150 ml of saturated sodium chloride solution.

The solution dried over magnesium sulphate was then evaporated to dryness under vacuum.

The residuary oil (13 g) was chromatographed on a silica column (200 g). Elution was first effected with (19/1) benzene-acetone mixture, which allowed various imurities to be eliminated, and then with a (4/1) benzene-acetone mixture, which provided 7.5 g of the crude product.

To obtain the product substantially pure, the crude product was dissolved in 50 ml of benzene. The solution was placed in a 250 ml flask and the solution was frozen by cooling in liquid nitrogen in contact with all the walls of the flask. The flask was then subjected to low vacuum (p <0.1 mm of mercury) and the flask was then removed from the liquid nitrogen, the cold produced by the evaporation being sufficient to maintain the mass in the solid state.

| Analysis: Calculated | C : 59.22 | H : 7.98 | N : 1.66 |
|---|---|---|---|
| Found | 59.84 | 7.94 | 1.57 |

The infrared spectrum in solution in chloroform shows a strong band at 1275 cm$^{-1}$ characteristic of the asymetric O—C—O group.

EXAMPLE 2

9-Ethoxycarbonyl midecamycine of Formula I above, in which $R_1 = C_2H_5$, $X = O$, $R_2 = H$.

Operating according to Example 1 using 15 g of Midecamycine, the methyl chloroformate was replaced with an equivalent quantity of ethyl chloroformate. The material was trated as indicated in Example 1; however the greater purity of the product did not require chromatography on silica. Finally, after evaporation of the benzene solution was previously indicated, a solid residue (13 g) was obtained. M.P. = 121° C.

| Analysis: Calculated | C : 59.64 | H : 8.09 | N : 1.58 |
|---|---|---|---|
| Found | 59.61 | 8.02 | 1.70 |

IR spectrum (potassium bromide tablet), strong band at 1260 cm$^{-1}$.

EXAMPLE 3

Butoxycarbonyl midecamycine of Fromula I above, in which $R_1 = C_4H_9$, $X = O$, $R_2 = H$.

Operating according to Example 1, the methyl chloroformate was replaced with butyl chloroformate. By the same treatment, a yellow powder (12 g) was obtained, M.P. = 75° C.

| Analysis: Calculated | C : 60.44 | H : 8.27 | N : 1.53 |
|---|---|---|---|
| Found | 60.55 | 8.46 | 1.39 |

IR spectrum (potassium bromide tablet), strong band at 1260 cm$^{-1}$.

EXAMPLE 4

9-Isobutoxycarbonyl midecamycine of Formula I, in which $R_1 = $ i-$C_4H_9$, $X = O$, $R_2 = H$.

Operating according to Example 1, the methyl chloroformate was replaced with isobutyl chloroformate. By the same treatment, a powder (8.4 g) was obtained, M.P. = 114° C.

| Analysis: Calculated | C : 60.44 | H : 8.27 | N : 1.53 |
|---|---|---|---|
| Found | 60.45 | 8.24 | 1.47 |

EXAMPLE 5

9-Phenoxycarbonyl midecamycine of Formula I in which $R_1 = C_6H_5$, $X = O$, $R_2 = H$.

4.06 g of Midecamycine was dissolved in 70 ml of acetone and 1.38 g of pyridine was added, then slowly a solution of 4.7 g of phenyl chloroformate in 30 ml of acetone. After the end of the addition, the mixture was left for 16 hours at the ambient temperature and then the mixture was poured into 500 ml of water. This was rendered alkaline to pH 8 by the addition of a 15% caustic soda solution and extracted 3 times with 200 ml of ethyl acetate. The organic solution was washed twice with 200 ml of saturated sodium chloride solution and then dried over magnesium sulphate and the solvent was evaporated under reduced pressure.

The residuary oil was chromatographed on a silica column and eluated with a (5/1) benzene-acetone mixture. 4 g of the product was thus obtained, which crystallised. After recrystallisation from petroleum ether, M.P. = 126° C.

| Analysis: Calculated | C : 61.72 | H : 7.66 | N : 1.50 |
|---|---|---|---|
| Found | 61.57 | 7.67 | 1.25 |

IR spectrum (in solution in chloroform), strong band at 1265 cm$^{-1}$.

EXAMPLE 6

9-Allyloxycarbonyl midecamycine of Formula I in which $R_1 = CH_2 = CH-CH_2$, $X = O$, $R_2 = H$.

Operating as in Example 1, the methyl chloroformate was replaced with allyl chloroformate. A white powder (9.6 g) was obtained, M.P. = 97° C.

| Analysis: Calculated | C : 60.18 | H : 7.97 | N : 1.56 |
|---|---|---|---|
| Found | 60.10 | 8.03 | 1.38 |

IR spectrum (in solution in chloroform), strong band at 1265 cm$^{-1}$.

EXAMPLE 7

9-Ethylthiocarbonyl midecamycine of Formula I in which $R_1 = C_2H_5$, $X = S$, $R_2 = H$.

Operating as in Example 1, the methyl chloroformate was replaced with S-ethyl-thiochloroformate. After chromatography, 6 g of product was obtained which crystallised from petroleum ether, M.P. = 121° C.

| Analysis: Calculated | C : 58.58 | H : 7.93 | N : 1.55 | S : 3.55 |
|---|---|---|---|---|
| Found | 59.00 | 8.04 | 1.43 | 3.57 |

IR spectrum (on potassium bromide tablets), strong bands at 1130 and 1168 cm$^{-1}$.

EXAMPLE 8

9-Propylthiocarbonyl midecamycine of Formula I in which $R_1 = C_3H_7$, $X = S$, $R_3 = H$.

Operating as in Example 7, the S-ethyl-thiochloroformate was replaced with S-propyl-thiochloroformate. 8.2 g of a product was obtained which crystallised from petroleum ether, M.P. = 128° C.

| Analysis: Calculated | C : 59.00 | H : 8.03 | N : 1.52 | S : 3.50 |
|---|---|---|---|---|
| Found | 59.05 | 8.14 | 1.42 | 3.66 |

IR spectrum (on potassium bromide tablet); strong bands at 1130 and 1168 cm$^{-1}$.

EXAMPLE 9

9-Methoxycarbonyl tetrahydromidecamycine of Formula I in which $R_1 = CH_3$, $X = O$, $R_2 = H$, saturated in 10,11 and 12,13.

Operating as in Example 1, tetrahydromidecamycine replaced the Midecamycine. 4.4 g of the desired product was obtained, M.P. = 86° C.

| Analysis: Calculated | C : 58.95 | H : 8.40 | N : 1.60 |
|---|---|---|---|
| Found | 59.15 | 8.41 | 1.46 |

IR spectrum (in solution in chloroform), strong band at 1280 cm$^{-1}$.

EXAMPLE 10

9-Ethoxycarbonyl tetrahydromidecamycine of Formula I in which $R_1 = C_2H_5$, $X = O$, $R_2 = H$, saturated in 10,11 and 12,13.

Operating as in Example 9, the methyl chloroformate was replaced with ethyl chloroformate. 4.3 g of the expected compound was obtained, M.P. = 82° C.

| Analysis: Calculated | C : 59.37 | H : 8.50 | N : 1.57 |
|---|---|---|---|
| Found | 59.67 | 8.59 | 1.39 |

IR spectrum (in solution in chloroform), strong band at 1275 cm$^{-1}$.

EXAMPLE 11

9-Butoxycarbonyl tetrahydromidecamycine of Formula I, in which $R_1 = C_4H_9$, $X = O$, $R_2 = H$, saturated in 10,11 and 12,13.

Operating as in Example 3, the Midecamycine was replaced with tetrahydromidecamycine. In the same manner, a yellow powder (6 g) was obtained, M.P. = 84° C.

| Analysis: Calculated | C : 60.17 | H : 8.67 | N : 1.53 |
|---|---|---|---|
| Found | 60.58 | 8.63 | 1.47 |

IR spectrum (in solution in chloroform), strong band at 1275 cm$^{-1}$.

EXAMPLE 12

9-Allyloxycarbonyl tetrahydromidecamycine of Formula I in which $R_1 = CH_2 = CH - CH_2 -$, $X = O$, $R_2 = H$, saturated in 10,11 and 12,13.

Operating as in Example 11, the butyl chloroformate was replaced with allyl chloroformate. A yellowish powder (3.2 g) was obtained, M.P. = 93° C.

| Analysis: Calculated | C : 59.92 | H : 8.38 | N : 1.55 |
|---|---|---|---|
| Found | 59.90 | 8.27 | 1.42 |

IR spectrum (in solution in chloroform), strong band at 1268 cm$^{-1}$.

EXAMPLE 13

9-Ethylthiocarbonyl tetrahydromidecamycine of Formula I in which $R_1 = C_2H_5$, $X = S$, $R_2 = H$ saturated in 10,11 and 12,13.

Operating as in Example 7, the Midecamycine was replaced with tetrahydromidecamycine. A yellowish powder (7.2 g) was obtained, M.P. = 96° C.

| Analysis: Calculated | C : 58.32 | H : 8.34 | N : 1.55 | S : 3.54 |
|---|---|---|---|---|
| Found | 58.37 | 8.14 | 1.49 | 3.37 |

IR spectrum (in solution in chloroform), strong bands at 1135 and 1165 cm$^{-1}$.

EXAMPLE 14

9-Ethoxycarbonyl-2'-acetyl midecamycine of Formula I in which $R_1 = C_2H_5$, $X = O$,

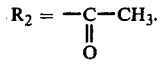

A mixture of 2.6 g of the compound of Example 2 and 3 g of acetic anhydride in 40 ml of pyridine was kept under reflux for 1 hour 30 minutes. Then 10 ml of methanol was added and reflux was continued for a further 15 minutes. The mixture was poured into 150 ml of water and rendered alkaline with dilute caustic soda solution to pH 8 to 9. The mixture was extracted twice with 100 ml of ethyl acetate and the organic phase was successively washed with 1 N hydrochloric acid solution, with saturated sodium bicarbonate solution, with water, dried over magnesium sulphate and the solvent evaporated under vacuum.

After filtration through an alumina column, the residue crystallised from an ether-hexane mixture. A lightly coloured solid (1.65 g) was obtained, M.P. = 239° C.

| Analysis: Calculated | C : 59.53 | H : 7.93 | N : 1.51 |
|---|---|---|---|
| Found | 59.58 | 7.92 | 1.38 |

IR spectrum (on potassium bromide tablets), strong bands at 1230 cm$^{-1}$ (acetate) and 1260 cm$^{-1}$ (carbonate).

The products according to to this invention have been studied as regards their pharmacological properties. In particular, their bacteriostatic action has been studied both "in vitro" and "in vivo" as well as the blood count results after oral administration.

"IN VITRO" BACTERIOSTATIC ACTION

This study was effected using Mueller-Hinton medium at pH 7 by the method using dilutions in frozen medium.

A series of half dilutions of the compounds to be studied was effected in order to obtain the contents of the medium of the culture of the active product ranging from 0.05 to 50 micrograms per ml. The media were seeded with gram$^+$ microbial strains. After remaining in the oven at 37° C. (24 to 48 hours), the minimal inhibitive concentrations or MICs were determined.

The results obtained with the products of this invention are set out in Table I below, in which also are given the results obtained with Midecamycine.

In Table II below, the results are given which were obtained with two of the compounds prepared, with a larger sample of gram$^+$ bacteria.

"IN VIVO" ANTIBACTERIAL ACTION

The anti-streptococcal and anti-diplococcal activity was determined by the action of these products on septicaemia in mice. The mice were infected by intraperitoneal injection of a solution of a streptococcal or diplococcal pneumonia culture broth. Treatment orally took place twice a day for three days and began 1 hour after inoculation of the germs.

For each dose of the product, a group of 10 mice were used and the mortality of the mice of each group was comapred with that of an infected but non-treated control group. The observation was pursued for 6 days.

In Table III below, the results are given which were obtained with 1 of the products of this study, the compound of Example 2, in comparison with Midecamycine.

MEASUREMENT OF PLASMATIC RATES

A — In Rats

The rats were divided into groups of four as homogeneous as possible and they had administered to them per os a known quantity of the product in suspension in colloidal (gum) water by means of a gastric probe. As a function of time, one group of rats were killed each time and the blood of each rat was taken individually by way of the mesenteric vein. After addition of a quantity of heparine, the plasma was separated by centrifuging.

Starting with the plasma thus isolated, dosage of the product by a biological procedure was effected. Operation was effected by the diffusion method in Mueller-Hinton medium at pH 8 on a test germ, Sarcinea Lutea ATCC 9341. The dosage was effected in a cupula. The plasma was put into contact with the germ and on the next day the diameter of inhibition was measured, from which there was deduced the concentration with respect to a control sample ranging from) 0.25 to 8 γ/ml.

In Table IV below are indicated the plasmatic rates obtained from the compound of Example 2 as administered in doses of 100 and 200 mg/kg per os and by comparison the results obtained with midecamycine administered in the same doses.

B — In Dogs

In the same manner, the plasmatic rates were determined which were obtained with dogs with a single dose of 400 mg of the compound of Example 2 administered orally. The results obtained are given in Table V in comparison with those obtained for an equal dose of Midecamycine.

The products of the invention can be utilised in medicine for the treatment of infections based on gram+ germs and in particular in the treatment of a staphylococcal and streptococcal infections.

They have been put up for administration orally (tablets, capsules, suspensions, oral gels etc.), by injection and by rectal administration.

By way of example, the following formulations can be indicated for the compound of Example 2.

| Capsules containing 200 mg | | |
|---|---|---|
| Compound of Example 2 | 200 | mg |
| Magnesium stearate | 5 | mg |
| for a No. 1 capsule | | |
| Tablets containing 200 mg | | |
| Compound of Example 2 | 200 | mg |
| Microcrystalline cellulose | 100 | mg |
| Amberlite IRP 88* | 20 | mg |
| Magnesium stearate | 10 | mg |
| for a 300 mg tablet | | |
| (* ion exchange resin made by Rohm & Haas) | | |
| Extemporaneous oral gel | | |
| Compound of Example 2 | 0.1 | g |
| Sodium saccharinate | 0.0013 | g |
| Sodium cyclamate | 0.02 | g |
| Glycamil | 0.002 | g |
| Sodium carboxymethyl cellulose (300 CPS) | 0.12 | g |
| Aerosil | 0.01 | g |
| Ground sugar | 4.1607 | g |
| Mannitol | 3.0 | g |
| Aromatiser | 0.586 | g | for an 8 g sachet for dilution with the contents of a teaspoonful of water.

TABLE I

Anti-bacterial Activity "in vitro" in μg/ml in solid medium

| | | | diacyl | Compound of Example No | | | | |
|---|---|---|---|---|---|---|---|---|
| Bacterial sample Gram Positive Germs | Midecamycine | 2 ethoxy carbonyl | 14 g-ethoxy carbonyl-2-acetyl | 3 Butoxy carbonyl | 1 Methoxy carbonyl | 4 Isobutoxy carbonyl | 7 Ethylthio carbonyl | 8 propyl thio carboxyl |
| Staphylococcus Londres | 0,8 | 0,8 | 0,8 | 0,8 | 0,8 | 0,8 | 1,56 | 0,8 |
| Staphylococcus Aureus 521 IP | 0,8 | 0,8 | 1,56 | 0,8 | 0,8 | 1,56 | 1,56 | 1,56 |
| Streptococcus Pyogenes GR. A 561 IP | 0,2 | 0,2 | 1,56 | 0,2 | 0,2 | 0,2 | 0,2 | 0,4 |
| Streptococcus Agalactiae GR. B 55 118 IP | 0,4 | 0,4 | 0,8 | 0,8 | 0,4 | 0,4 | 0,8 | 1,56 |
| Streptococcus Faecalis GR. D A 23 | 0,4 | 0,4 | 0,8 | 0,8 | 0,4 | 0,4 | 0,8 | 0,8 |
| Sarcina Lutea ATCC 9 341 | 0,8 | 0,8 | 1,56 | 1,56 | 0,8 | 1,56 | 1,56 | 1,56 |
| Bacillus Cereus ATCC 9 634 | 0,4 | 0,4 | 0,8 | 0,8 | 0,4 | 0,8 | 0,8 | 1,56 |
| Bacillus Subtilis ATCC 6 633 | 0,8 | 0,8 | 0,8 | 1,56 | 0,8 | 0,8 | 0,8 | 1,56 |
| Listeria Monocytogenes 5 734 | 0,8 | 0,8 | 0,8 | 1,56 | 0,8 | 1,56 | 1,56 | 1,56 |
| Corynebacterium Abbott | 0,4 | 0,2 | 0,4 | 0,4 | 0,2 | 0,4 | 0,4 | 0,8 |

| | Compound of Example No. | | | | | | |
|---|---|---|---|---|---|---|---|
| Bacterial sample Gram Positive Germs | 9 | 5 | 6 | 10 | 11 | 13 | 12 |
| Staphylococcus Londres | 1,56 | 0,8 | 0,8 | 1,56 | 3,12 | 3,12 | 1,56 |
| Staphylococcus Aureus 521 IP | 3,12 | 1,56 | 1,56 | 3,12 | 6,2 | 3,12 | 3,12 |
| Streptococcus Pyogenes GR. A 561 IP | 0,4 | 0,2 | 0,2 | 0,8 | 0,8 | 0,8 | 0,4 |
| Streptococcus Agalactiae GR. B 55 118 IP | 1,56 | 0,8 | 0,8 | 1,56 | 3,12 | 3,12 | 1,56 |
| Streptococcus Faecalis GR. D A 23 | 0,8 | 0,4 | 0,8 | 1,56 | 3,12 | 3,12 | 3,12 |
| Sarcina Lutea ATCC 9 341 | 3,12 | 1,56 | 1,56 | 3,12 | 3,12 | 3,12 | 3,12 |
| Bacillus Cereus ATCC 9 634 | 1,56 | 0,8 | 0,8 | 1,56 | 3,12 | 3,12 | 1,56 |
| Bacillus Subtilis ATCC 6 633 | 1,56 | 0,8 | 0,8 | 1,56 | 3,12 | 3,12 | 1,56 |
| Listeria Monocytogenes 5 734 | 1,56 | 0,8 | 0,8 | 1,56 | 3,12 | 3,12 | 3,12 |
| Corynebacterium Abbott | 0,8 | 0,4 | 0,4 | 0,8 | 1,56 | 1,56 | 1,56 |

TABLE II

| | M.I.C. μg / ml | | |
|---|---|---|---|
| GERMS | Midecamycine | Composition of Example 1 mono | Composition of Example 14 di |
| Staphylococcus Londres | 0,4 | 0,4 | 0,4 |
| Staphylococcus 209 IP | 0,4 | 0,4 | 0,4 |

TABLE II-continued

| | M.I.C. μg / ml | | |
|---|---|---|---|
| GERMS | Midecamycine | Composition of Example 1 mono | Composition of Example 14 di |
| Staphylococcus Aureus Gervais D 319 | 0,8 | 0,8 | 0,8 |
| Staphylococcus Aureus E 120 | 0,8 | 0,8 | 1,56 |
| Staphylococcus Albus P C I J 200 | 0,8 | 0,8 | 1,56 |
| Streptococcus Pyogenes gr A 561 IP | 0,2 | 0,2 | 0,4 |
| Streptococcus Pyogenes gr A D 313 | 0,2 | 0,2 | 0,2 |
| Streptococcus Agalactiae gr B | 0,4 | 0,4 | 0,4 |
| Streptococcus Pyogenes gr C | 1,56 | 1,56 | 1,56 |
| Streptococcus Faecalis var. Zymogenes | 1,56 | 0,8 | 0,8 |
| Streptococcus Faecalis gr D 5 434 IP | 0,4 | 0,4 | 0,4 |
| Streptococcus Faecalis gr D F 262 | 1,56 | 1,56 | 1,56 |
| Sarcina Lutea ATCC 9341 | 0,1 | 0,1 | 0,1 |
| Listeria Monocytogenes 5 844 IP | 0,8 | 0,8 | 0,8 |
| Listeria Monocytogenes Ramisse type IV | 1,56 | 1,56 | 1,56 |
| Listeria Monocytogenes Joubert E 102 | 0,8 | 0,8 | 0,8 |
| Erysipelothrix Insidiosa E 159 | 0,8 | 0,8 | 0,8 |
| Erysipelothrix Insidiosa A 27 | 0,8 | 0,8 | 0,8 |
| Bacillus Cereus ATCC 10 702 | 0,4 | 0,4 | 0,8 |
| Bacillus Cereus ATCC 9 634 | 0,4 | 0,4 | 0,8 |
| Bacillus Subtilis Leugar A 156 | 0,4 | 0,4 | 0,8 |

TABLE III

| | Dose | P. 100 of survival at 6th day | |
|---|---|---|---|
| Product | mg/kg × 6 j. | Diplococcus | Streptococcus |
| Control | 0 | 0 | 0 |
| Composition of | 200 | 50 | 70 |
| Example 2 | 400 | 100 | 100 |
| Midecamycine | 200 | 20 | 40 |
| | 400 | 80 | 100 |

TABLE IV

| | Dose administered 100 mg / kg | | Dose administered 200 mg / kg | |
|---|---|---|---|---|
| Time of Treatment (in minutes) | Composition of Example 2 (μg/ml) | Midecamycine (μg/ml) | Composition of Example 2 (μg/ml) | Midecamycine (μg/ml) |
| 30 | 1,61 | 0,39 | 9,43 | 2,45 |
| 120 | 4,52 | 2,43 | 9,57 | 6,82 |
| 180 | 3,8 | 1,87 | 7,27 | 8,23 |
| 240 | 1,88 | 1,4 | 7,6 | 5,54 |
| 300 | 1,29 | 1 | 3,4 | 4,2 |
| 420 | 0,54 | 0,26 | — | — |

TABLE V

| | Plasmatic rate in dogs Single dose of 400 mg per os | |
|---|---|---|
| Time of Treatment after administration | Concentration in μg/ ml plasma | |
| | Composition of example 2 | Midecamycine |
| 30 minutes | 3,4 | 0,96 |
| 60 minutes | 2,84 | 3,2 |
| 90 minutes | 2,22 | 2,46 |
| 120 minutes | 1,46 | 1,34 |
| 180 minutes | 0,84 | 1,1 |
| 240 minutes | 0,6 | 0,78 |
| 300 minutes | 0,46 | 0,46 |
| 420 minutes | 0,23 | 0,18 |

We claim:
1. Compounds represented by the formula:

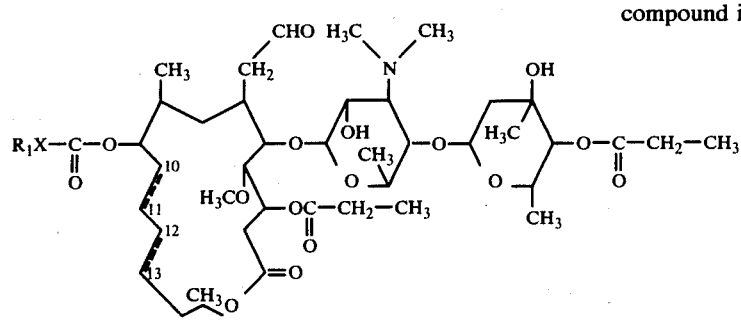

in which

X is selected from the class of oxygen and sulphur, $R_1$ is selected from the group consisting of alkyl of 1 to 5 carbons, isobutyl, allyl and phenyl, the broken lines indicating the optional presence of double bonds with the proviso that the two double bonds in the 10, 11 position on the one hand and 12, 13 on the other, exist simultaneously or neither of them exists.

2. The compound according to claim 1 wherein said compound is 9-methoxycarbonyl midecamycine.

3. The compound according to claim 1 wherein said compound is 9-ethoxycarbonyl midecamycine.

4. The compound according to claim 1 wherein said compound is 9-butoxycarbonyl midecamycine.

5. The compound according to claim 1 wherein said compound is 9-isobutoxycarbonyl midecamycine.

6. The compound according to claim 1 wherein said compound is 9-phenoxycarbonyl midecamycine.

7. The compound according to claim 1 wherein said compound is 9-allyloxycarbonyl midecamycine.

8. The compound according to claim 1 wherein said compound is 9-ethylthiocarbonyl midecamycine.

9. The compound according to claim 1 wherein said compound is 9-propylthiocarbonyl midecamycine.

10. The compound according to claim 1 wherein said compound is 9-methoxycarbonyl tetrahydromidecamycine.

11. The compound according to claim 1 wherein said compound is 9-ethoxycarbonyl tetrahydromidecamycine.

12. The compound according to claim 1 wherein said compound is 9-butoxycarbonyl tetrahydromidecamycine.

13. The compound according to claim 1 wherein said compound is 9-allyloxycarbonyl tetrahydromidecamycine.

14. The compound according to claim 1 wherein said compound is 9-ethylthiocarbonyl tetrahydromidecamycine.

15. An antibiotic medicament comprising, as its active ingredient, an antiobiotic effective concentration of the compound represented by the formula:

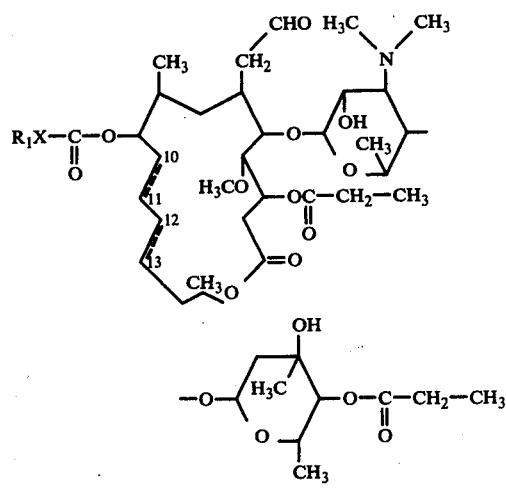

in which X is selected from the class of oxygen and sulphur. $R^1$ is selected from the group consisting of alkyl of 1 to 5 carbons, isobutyl, allyl and phenyl and $R_2$ is selected from the group consisting of hydrogen and acetyl, the broken lines indicating the optional presence of double bonds with the proviso that the two double bonds, in the 10, 11 position on the one hand and 12, 13 on the other, exist simultaneously or neither of them exists.

16. A antibiotically composition which contains the compound of claim 1 as an active ingredient, in a pharmaceutically effective concentration associated with a pharmaceutical vehicle for oral, rectal or parenteral administration.

17. The process which comprises reacting a midecamycine compound selected from the class consisting of midecamycine or tetrahydromidecamycine with a chloroformate or thiochloroformate of the formula:

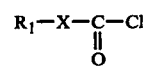

in which X is selected from the class consisting of oxygen and sulphur and $R_1$ is selected from the class consisting of alkyl of 1 to 5 carbons, isobutyl, allyl and phenyl in pyridine and further reacting the resultant product with acetic anhydride in pyridine to obtain a product of the following structure:

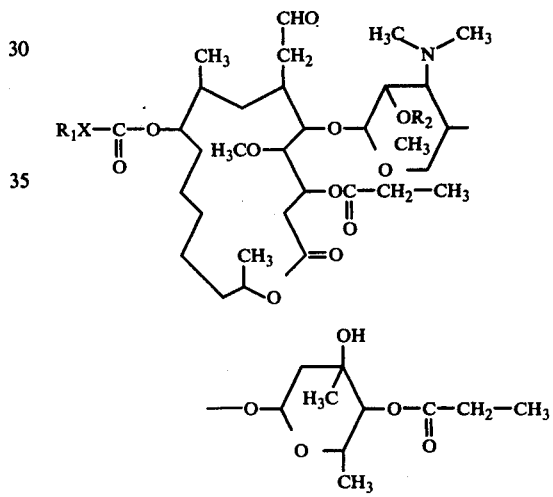

wherein $R_2$ is acetyl.

* * * * *

UNITED STATES PATENT AND TRADEMARK OFFICE
CERTIFICATE OF CORRECTION

PATENT NO. : 4,141,971

DATED : February 27, 1979

INVENTOR(S) : Francois Krausz and Alain Calvet

It is certified that error appears in the above-identified patent and that said Letters Patent are hereby corrected as shown below:

Correct the abstract drawing and the drawing on the center of Column 1 by adding --$CH_3$--, as follows:

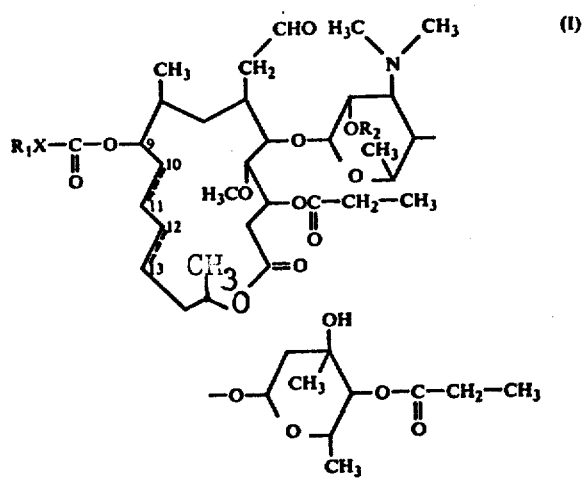

IN THE SPECIFICATION:

Column 2, line 59 correct the spelling of [imurities] to read --impurities--.

Column 3, line 21, before [was] insert --as--.

UNITED STATES PATENT AND TRADEMARK OFFICE
CERTIFICATE OF CORRECTION

PATENT NO. : 4,141,971

DATED : February 27, 1979

INVENTOR(S) : Francois Krausz and Alain Calvet

It is certified that error appears in the above-identified patent and that said Letters Patent are hereby corrected as shown below:

IN THE CLAIMS:

Claim 15, correct the drawing by substituting for [H], --$R_2$--, as follows:

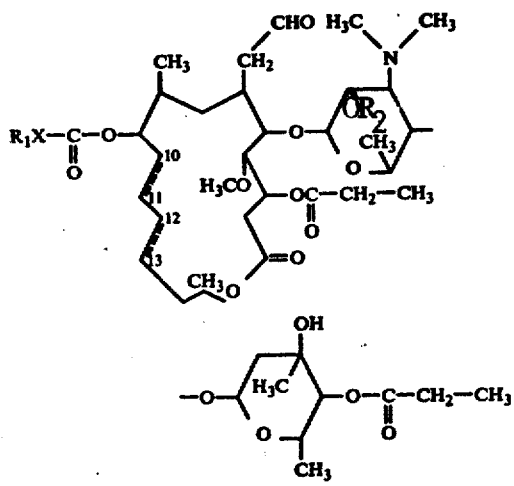

Claim 16, column 16, first line, change [antibiotically] to --antibiotical--.

Claim 17, column 12, line 26, change [pyrindine] to --pyridine--.

UNITED STATES PATENT AND TRADEMARK OFFICE
CERTIFICATE OF CORRECTION

PATENT NO. : 4,141,971

DATED : February 27, 1979

INVENTOR(S) : Francois Krausz and Alain Calvet

It is certified that error appears in the above-identified patent and that said Letters Patent are hereby corrected as shown below:

Claim 17, correct the drawing by adding a lead line from "$CH_3$", as follows:

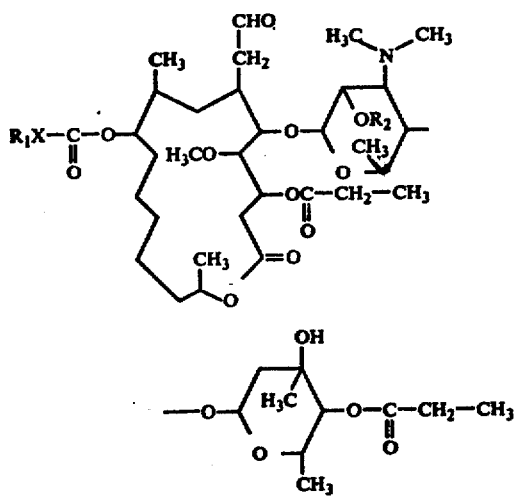

Signed and Sealed this

Eighth Day of July 1980

[SEAL]

Attest:

SIDNEY A. DIAMOND

Attesting Officer

Commissioner of Patents and Trademarks